(12) United States Patent
Benda

(10) Patent No.: US 6,773,682 B1
(45) Date of Patent: *Aug. 10, 2004

(54) APPARATUS AND METHOD FOR PURIFYING AIR

(75) Inventor: George Benda, Itasca, IL (US)

(73) Assignee: Artos Technology, Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/405,781

(22) Filed: Sep. 27, 1999

(51) Int. Cl.$^7$ ................................................. B01J 19/12
(52) U.S. Cl. .................................... 422/186.3; D23/364
(58) Field of Search ........................... 422/186.3, 186.8; 445/22; D23/351, 355, 364

(56) References Cited

U.S. PATENT DOCUMENTS

| | | | |
|---|---|---|---|
| 3,844,741 A | * 10/1974 | Dimitrik | 422/186.3 |
| 5,564,065 A | 10/1996 | Fleck et al. | 422/186.3 |
| 5,601,786 A | 2/1997 | Monagan | 422/108 |
| 5,707,915 A | 1/1998 | Taoda | 502/159 |
| 5,779,912 A | 7/1998 | Gonzalez-Martin et al. | 210/748 |
| 5,835,840 A | * 11/1998 | Goswami | 422/186.3 |
| 5,874,701 A | 2/1999 | Watanabe et al. | 204/157.15 |
| 5,919,422 A | 7/1999 | Yamanaka et al. | 422/121 |
| 5,933,702 A | 8/1999 | Goswami | 422/186.3 |
| 5,945,372 A | * 8/1999 | Landgraf et al. | 502/350 |
| 5,948,355 A | * 9/1999 | Fujishima et al. | 422/186.3 |
| 6,135,838 A | * 10/2000 | Wang | 445/22 |

OTHER PUBLICATIONS

Copending Application 09/928,461.*

* cited by examiner

*Primary Examiner*—James J. Seidleck
*Assistant Examiner*—Thao Tran
(74) *Attorney, Agent, or Firm*—Clifford Kraft

(57) ABSTRACT

An apparatus and method of purifying air where a photocatalyst is exposed to ambient air to purify it from bacteria, hydrocarbons, and volatile organic compounds. The apparatus can contain a vertical reactor containing the photocatalyst either on sheets, in a web-like structure, or in a fibrous mass, or any other way of holding it. The photocatalyst can be excited with an ultraviolet light source. Air rises through the reactor by natural convection caused by a heater or heater element located in the reactor. The apparatus can contain no moving or replaceable parts. An optional air filter can also be located at the bottom of the reactor to remove particulate matter from the rising air. In one embodiment, excess visible light from the ultraviolet light source is allowed to escape from the top, bottom, or side of the device to provide light for persons to see at night thereby acting as a night light which simultaneously purifies air. The invention also comprises a method where cooler ambient air is allowed to enter a chimney or reactor and flow upward past a heater by natural convection, also flowing past an excited photocatalyst thereby being purified from contaminants such as bacteria and organic compounds.

16 Claims, 7 Drawing Sheets

APPARATUS AND METHOD FOR PURIFYING AIR

BACKGROUND

1. Field of the Invention

This invention relates generally to the field of air quality and more particularly to an apparatus and method for purifying air.

2. Description of Related Art

Air purifiers generally consist of filter units driven by fans. The filters may be particulate filters followed by activated charcoal or other filter types. In general, the fans are noisy, and the filters need often replacement.

Some devices have been built using photocatalysts activated by ultraviolet light. In general these have been wall panels, or filter devices again driven by fans. U.S. Pat. No. 5,919,422 teaches a number of configurations where ambient air in a container simply reacts with the photocatalyst by diffusion. This method will work for a small container, but needs the addition of a fan to purify air in an entire room. U.S. Pat. No. 5,945,372 teaches a photocatalyst used in building HVAC systems (with large fans) to purify air in buildings.

What is badly needed is a small device that can be directly plugged into a wall electrical socket that contains no moving or replaceable parts. This device should, over a period of hours, purify the air in a room by killing bacteria, removing organic compounds, and possibly even converting poisons such as carbon monoxide into something more harmless such as carbon dioxide. The device must be quiet, since it would be left in a room both day and night. Its purifying element must never need replacement. It must not produce too much heat, and it should not need any maintenance.

SUMMARY OF THE INVENTION

The present invention relates to an apparatus and method for purifying air in a room. The invention causes air to pass through a vertical passageway or chimney (reactor) that contains a photocatalyst that is activated by an ultraviolet light source. Air is caused to move by a process called natural convection whereby no external force such as a fan needs to be used. Natural convection occurs when air is heated by a hot body and hence becomes less dense than colder surrounding air. The less dense air experiences an increase in upward buoyancy force which causes it to move upward. The present invention can contain a small heater or heat element in a vertical passageway or chimney (reactor). Cold air can enter the apparatus through slots or openings at the bottom of the device. An optional filter can be placed here to remove particulate matter. A heater or heat element can be placed above the air entrance port or filter if a filter is present. This heater causes natural convection to take place. As the warmer air moves upward, a pressure gradient is formed which in turn draws more cool air into the device.

The slightly heated air passes up through the chimney or reactor passageway where it encounters a photocatalyst such as titanium dioxide either in pure form or doped with any of several metals. The photocatalyst is activated by an ultraviolet light source that emits light with a wavelength or spectrum shorter than 387 nanometers (which is the activation energy of pure titanium dioxide in the anatase crystal form), or shorter than the activation energy of whatever catalyst is used.

The photocatalyst is held in the chimney in a form which exhibits a large surface area to allow maximum exposure of the air that is convecting upward. The photocatalyst can be coated on a flat sheet which in turn can be spiraled on a loose spool to obtain more surface area of exposure, or the photocatalyst can be impregnated on fibers which can be formed into a fibrous mass (an example of such fibrous mass might be fiberglass insulation or a like fiber). The fibers can be natural or synthetic organic materials, or can be glass such as fiberglass. Any means of holding the photocatalyst in position so that air passing upward in the chimney makes contact with it is within the scope of the present invention.

The ultraviolet light source that is used to activate the photocatalyst can be a commercial UV light bulb, a fluorescent lamp (which leaks considerable UV light), or a means of allowing sunlight to enter the device. If a UV bulb is used, an optional power supply usually must be used to supply the bulb voltage.

The present invention contains an exit port on its top which can be slots or a small jet to allow the upward convecting air to re-enter the room. This port can contain an optional baffle to prevent UV light from entering an observer's eyes. This type of protection is necessary if wavelengths shorter than about 340 nanometers are used. It may also be desirable in some cases to prevent any visible light produced by the UV source from exiting the device. In other cases, it may desirable to allow visible light to exit the device so that the present invention can also be used as a night light while it purifies the air.

The present invention can be equipped with two electrical prongs on its back side so that it can be directly plugged into a standard 110 V. electrical outlet, or, optionally, it can have a power cord. Power from the electrical outlet can be used to supply energy to both the heater and to the ultraviolet light source. The direct electrical connection is optional since the present invention can also be run directly from batteries.

The present invention purifies air in a room over a span of hours since the rate of natural convection is slow. The invention can kill bacteria and can convert organic compounds such as volatile organics (VOC's), odor causing organics, hydrocarbons, and other undesirable compounds into smaller, less harmful or odorous, compounds such as carbon dioxide, water.

DETAILED DESCRIPTION

Figure 1:
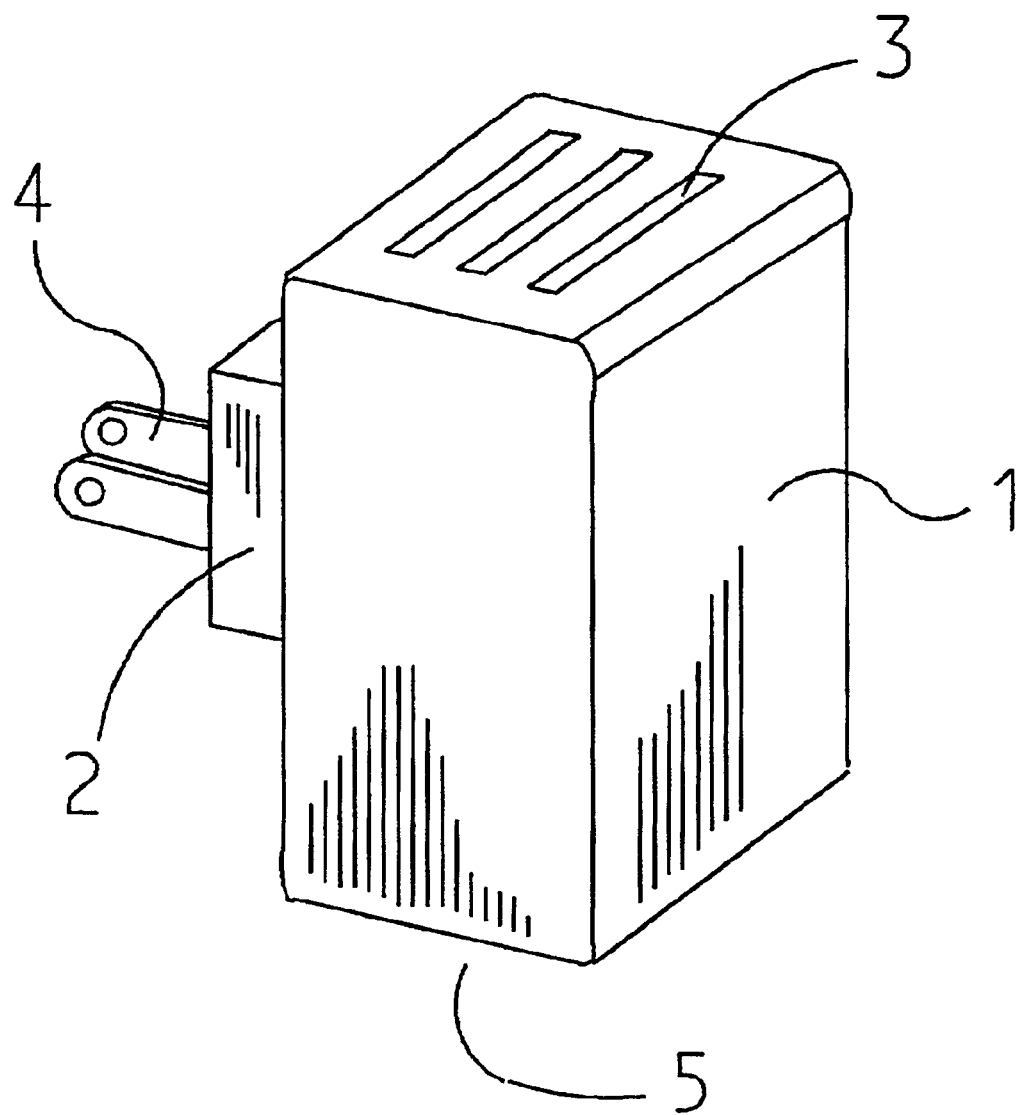
FIG. 1 shows a perspective view of an embodiment of the present invention. Electrical prongs are clearly seen.

Turning to FIG. 1, a perspective view of one embodiment of the present invention is seen. The unit can be made small enough to plug directly into an electrical outlet. The unit can contain electrical power prongs 4 on its backside for this purpose. Of course, it could be equipped with a power cord for normal plug-in. I could also use a wall plug transformer with a low voltage cord to the unit, or it could use batteries.

The unit can be housed in a plastic shell 1 for lightness and appearance. The shell or enclosure can however be any material including, but not limited to, plastic, wood, metal, or any other rigid material. Several holes or slots 3 can be provided on the top of the unit for purified air to exit the invention. These can be holes, slots, a nozzle, or any other means for air to exit the enclosure 1. The unit is also provided with slots, a hole, or any other means for contaminated air to enter the enclosure at the bottom. This entrance port 5 cannot be seen in FIG. 1.

The power prongs 4 can be directly connected to a power module or power supply 2. While this module 2 is shown external to the enclosure 1 in FIG. 1, it should be noted that this power supply or module can be inside the enclosure 1 so that the back of the unit is flat.

Figure 2:
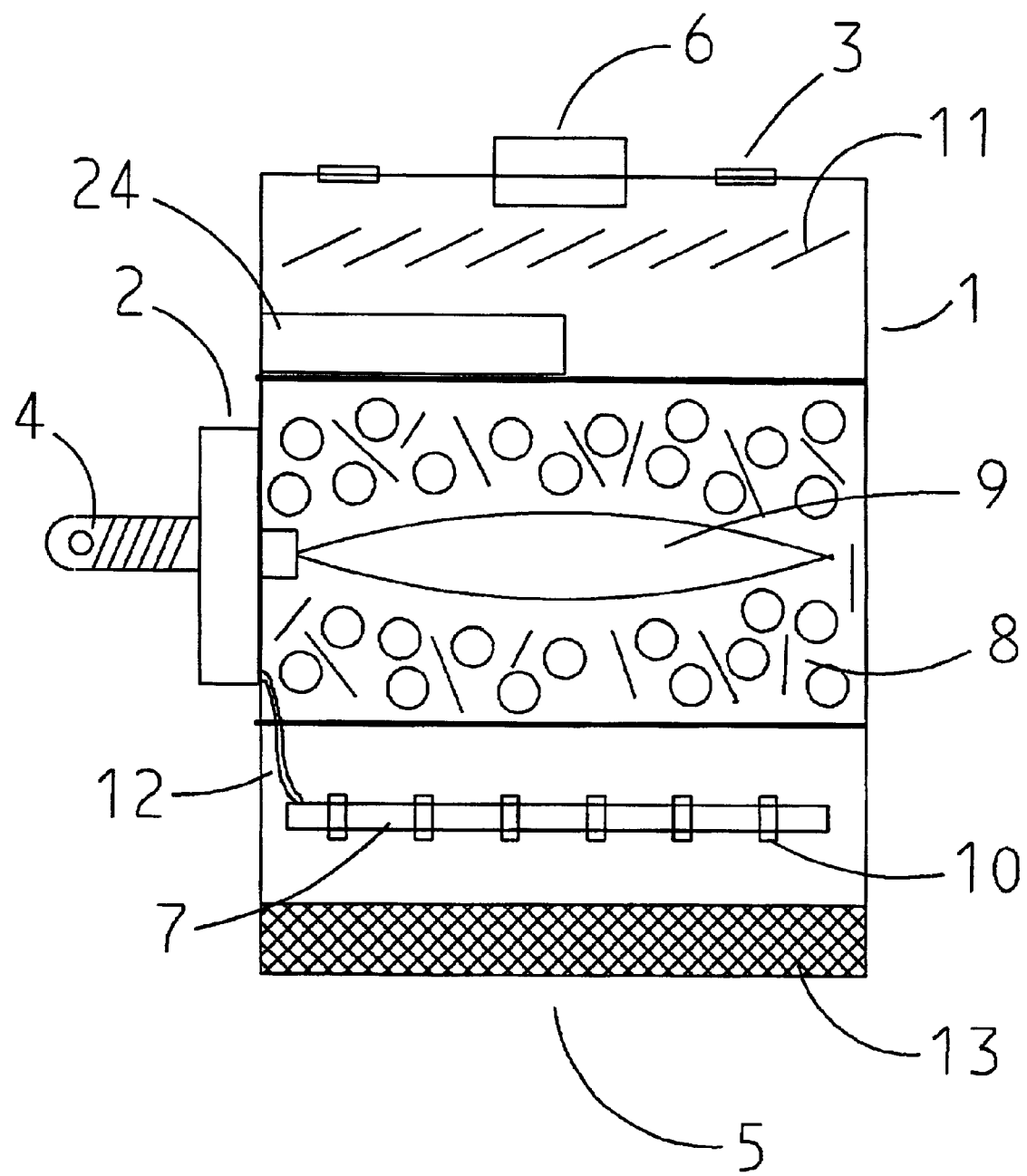
FIG. 2 shows a cut-away diagram of the interior of a particular embodiment.

FIG. 2 shows a cut-away diagram of the interior of an embodiment of the present invention. The electrical prongs 4 and power module 2 are again seen. Contaminated air can enter the bottom the unit through slots or any type of entry port of entry means 5. A heater pad 7 heats this air, and the air rises by natural convection. The heater pad 7 can be porus or permeable, or made in a type of weave so that air can readily pass through it. FIG. 2 shows holes or passageways 10 in the heater pad 7. Actual holes or passageways are not necessary if the pad is porus or permeable or a weave. The heater pad is attached to the power module 2 by a set of wires 12 that supply it with power. Any type of heater is within the 'scope of the present invention; however, the preferred heater supplies a constant flow of heat energy maintaining a surface temperature between 40 degrees C. to 70 degrees C. While hotter pads can be used, they can present a danger of fire, or a danger of heating the air hot enough that it might cause a burn if a person were to put their hand in the flow, etc. Also, since the purpose and objective of the present invention is to purify air over a prolonged period, it is not necessary to heat the air too hot in order to sufficiently purify the air in a room.

An optional filter 13 can be provided in the reactor to remove larger particulate matter. It should be noted that such a filter is an additional feature, and is not required for the functioning of the present invention. The enclosure 1 forms a chimney for the upward air flow. An internal chimney can be used if it is necessary to more accurately direct the flow; however, this may not be necessary. In this chimney, is a photocatalyst 8 that is either impregnated on a surface, or is attached to a fibrous mass of material. It is very important for the photocatalyst to display a large surface area to the upward air flow. The most common photocatalyst is titanium dioxide (TiO2). The most convenient form of TiO2 is the anatase crystal form; however, the rutile form can be used. It is well known that the rutile form does not display as much surface area as the anatase form. While TiO2 is the preferred photocatalyst, any other photocatalyst capable of killing bacteria and decomposing organic molecules is within the scope of the present invention.

The photocatalyst can be doped to increase its efficiency or it can be used in its pure form. The most common doping material is platinum (Pt) metal; however, numerous other dopants are known in the art. It is also known that TiO2 becomes more efficient in the presence of a hydroxyl ion (OH—). It is within the scope of the present invention to use a means of maintaining a humidity of 40% or higher; however, it is highly desirable to avoid such a device since one of the objectives of the present invention is a unit that never needs servicing. TiO2, works well when photo-excited to kill bacteria and convert organic compounds at humidities as low as 30%, especially if it is doped.

In the region of the chimney 1, where the catalyst is exposed to the air rising past its surface by natural convection, is an ultraviolet (UV) light source 9. The activation energy of pure anatase TiO2 is 387 nanometers; thus, any ultraviolet source can be used that supplies light with wavelengths shorter or equal to 387 nanometers (or alternatively shorter than the activation energy of any catalyst that is used). It is well known in the art, that commercial black lights, and even commercial fluorescent bulbs of various colors emit a considerable amount of UV light down to about 350 nanometers. This light is highly suitable to excite the photocatalyst 8 in the present invention and is safe to human eyes. Shorter wavelengths can be used; however, if shorter wavelengths are used, suitable eye protection should be provided. FIG. 2 shows a set of light baffles 11 that are present simply to protect eyes if shorter wavelengths are used. These optional baffles 11 can also be used to prevent the escape of visible light if desired.

In one embodiment of the present invention, the baffles 11 are not present, and a UV light source 8 of wavelength no shorter than around 350 nanometers is used. The visible portion of the source's output is purposely allowed to escape from the top or side of the device so that the device can be used as a night light, for example in a bathroom, while simultaneously purifying air.

Purified air, after having passed the photocatalyst 8 can escape from the top of the unit by either slots 3, or a nozzle 6 or any other means of escape. Generally, only one of these escape means will be used; however, any combination can be used if needed.

An optional feature, which is usually not necessary, is a means for controlling humidity 24 of the air passing the photocatalyst. This can be a small reservoir and wick, or any other means of increasing humidity.

Figure 3:
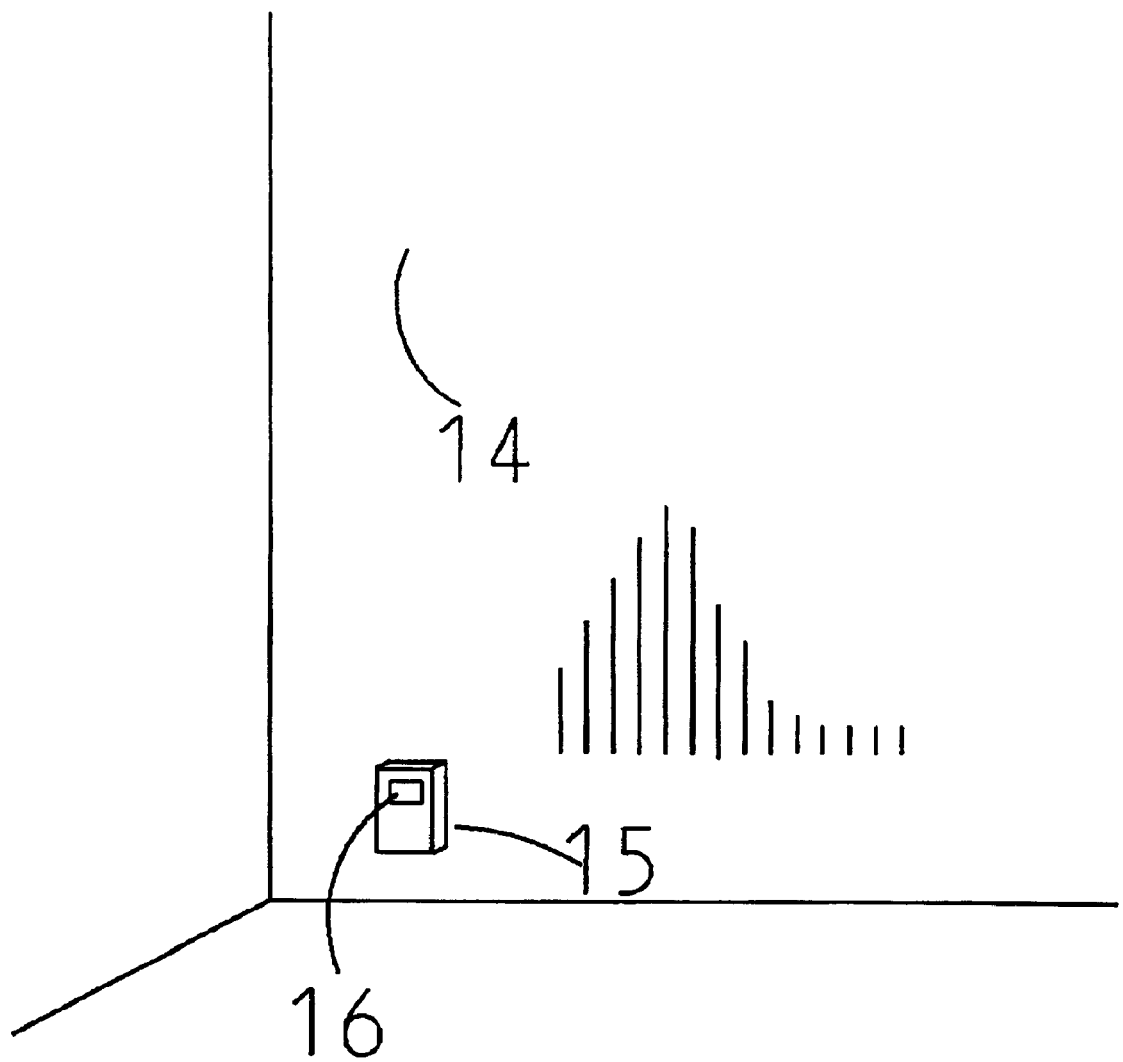
FIG. 3 shows an embodiment of the present invention as it is used to purify air in a room.

FIG. 3 shows an embodiment of the present invention 15 plugged into an electrical outlet (behind the device) in the corner of a room 14. The device provides a method of purifying air by heating it at the bottom of the enclosure so that it rises by natural convection up through the device passing a photo-excited photocatalyst and then back into the room from the top of the device. An optional window 16 can be provided on the front, top, or side of the device to allow visible light to also exit the device. The present invention thus can plug into any convenient power outlet, and immediately begin purifying air in the room, removing odors, volatile organics, and other chemicals, as well as killing airborne bacteria. In addition, as mentioned, in some embodiments of the invention, visible light is allowed to escape so that the device also functions as a night light.

Figure 4:
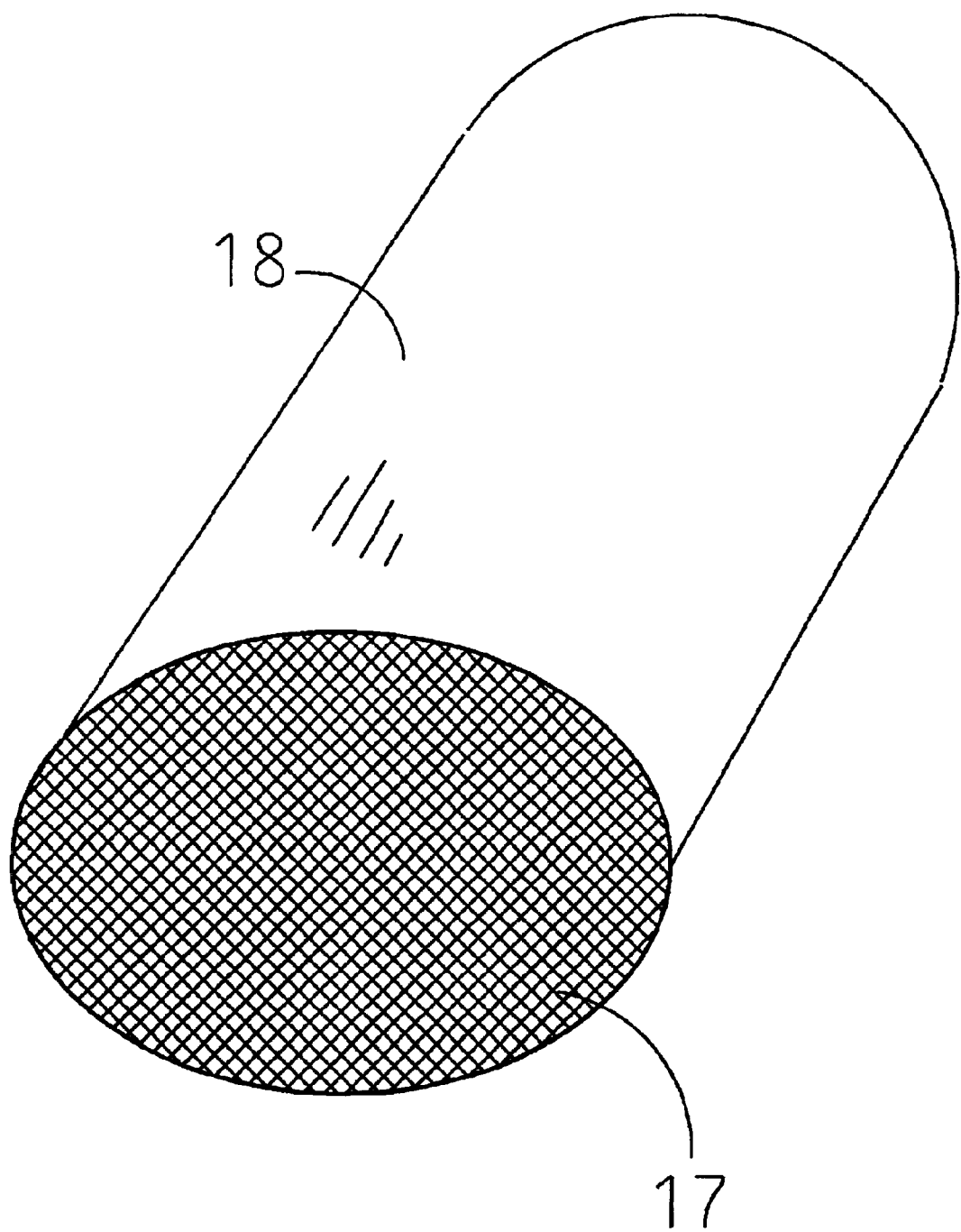
FIG. 4 shows a corrugated tube means for holding catalyst.

FIG. 4 shows a means for containing the photocatalyst in a corrugated tube or container 18. The shape shown in FIG. 4 is a cylinder; however, any shape is within the scope of the present invention. Here the cross-section 17 contains a honeycomb of tubes or cells which have catalyst coated or otherwise attached to their walls. Any means of attaching the catalyst is within the scope of the invention. Discrete tubes can be used with catalyst coated on the inside and outside. For this embodiment, light must shine into the tubes or honeycomb to excite the photocatalyst.

Figure 5:
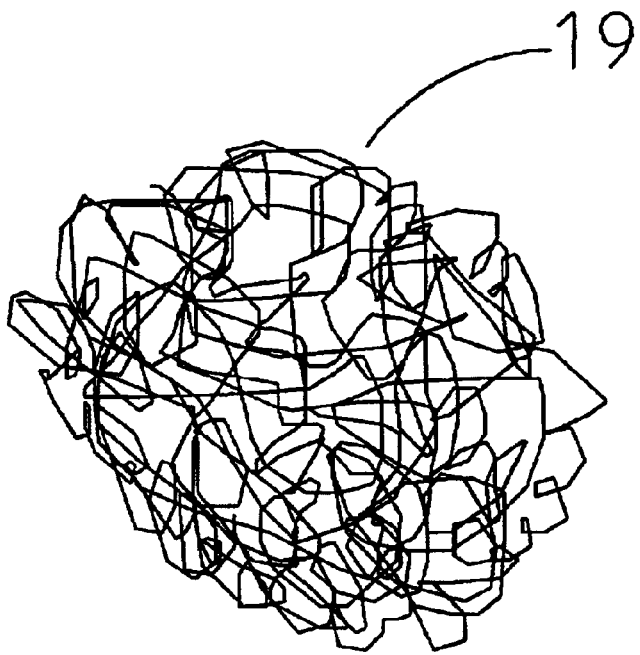
FIG. 5 shows a fibrous mass holding catalyst.

FIG. 5 shows catalyst impregnated into a fibrous bundle 19 made of fine strands of material. The strands can be any rigid material or fiber capable of being made into strands. One material that can be used is fiber glass. Another possible material is paper with the photocatalyst impregnated into its fibers. In this case, the rising air passes through the paper and is purified as it contacts the excited photocatalyst. In this case, the principle is similar to a paper filter.

Figure 6:
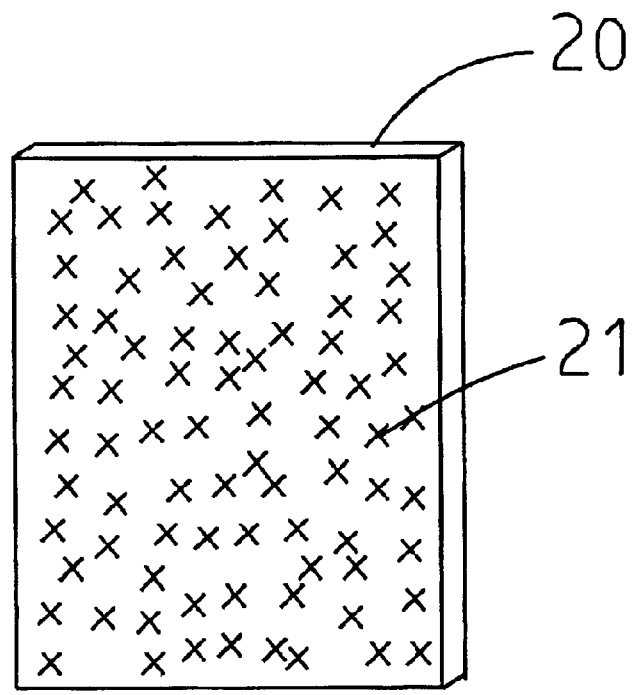
FIG. 6 shows catalyst attached to a plate.

FIG. 6 shows catalyst 21 attached to the surface of a plate 20. Any method of attachment can be used and is within the scope of the present invention including, but not limited to, plating, attaching with adhesive, impregnating, sputtering, diffusing, or any other attachment method. The plate 20 can be metal, plastic, wood, glass, paper or any other rigid or semi-rigid material. While a plate is shown in FIG. 6, the catalyst can be attached to a very thin sheet, and to increase surface area, that sheet can be rolled into a loose spiral or any other shape, shapes being chosen to maximize exposed surface area.

Figure 7:
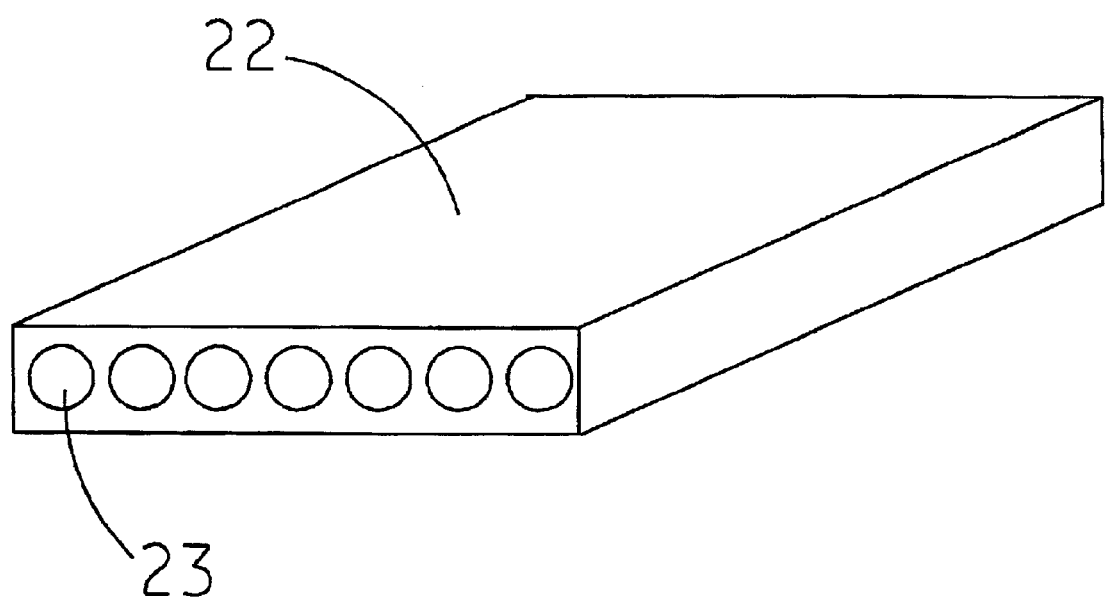
FIG. 7 shows catalyst in tubes in a structure.

FIG. 7 shows a system of tubes 23 in a structure 22. The tubes can be coated with catalyst on either the inside, the outside, or both the inside and outside. Any method of attaching the catalyst to the tube surface is within the scope of the present invention, and any type or material of tube is within the scope of the present invention.

Figure 8:
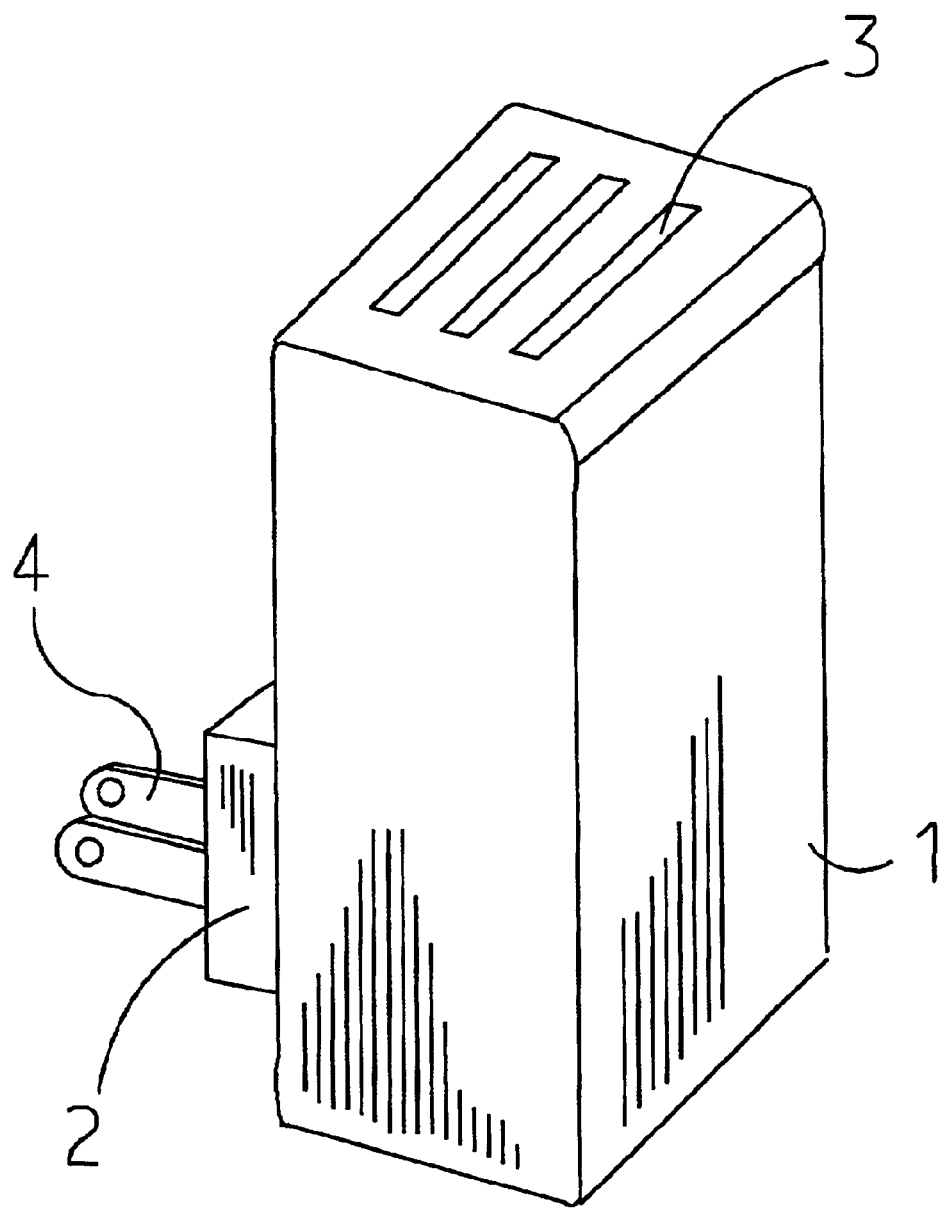
FIG. 8 shows an embodiment equipped with an elongated chimney or reactor.

FIG. 8 shows an embodiment of the present invention that is considerably taller (extends more vertically) than other embodiments. This embodiment also contains an outer case 1 and a means on its top for heated, purified air to escape 3. Again the optional power prongs 4 and an optional power supply 2 can be seen. The difference between this embodiment and the on shown in FIG. 1 is that with a taller chimney or reactor, more photocatalyst can be exposed to the rising air (the air stays in the vicinity of the catalyst for a longer period of time before exiting the device). A unit such as that shown in FIG. 8 purifies air faster than a smaller unit. In all other respects, the embodiment shown in FIG. 8 is similar to that shown in FIG. 1.

It should be noted that the embodiments disclosed are for purposes of illustration of the principles of the invention. Many other embodiments and realizations may be made without deviating from the scope of the present invention. Many materials can be substituted for the ones named in the disclosed embodiments; any material with similar properties to the one disclosed is within the scope of the present invention.

I claim:

1. A device for purifying air comprising:

a reactor;

a photocatalyst located in said reactor;

an ultraviolet light source located in said reactor, said ultraviolet source illuminating said photocatalyst;

a heater means located in said reactor for drawing air into said reactor by convection and causing said air to rise past said photocatalyst before being expelled.

2. The device for purifying air of claim 1 further comprising a pair of electrical prongs protruding from said device, said electrical prongs allowing said device to be directly plugged into an electrical outlet.

3. The device for purifying air of claim 1 wherein said photocatalyst is primarily titanium dioxide.

4. The device for purifying air of claim 3 wherein said titanium dioxide is doped with a dopant.

5. The device for purifying air of claim 4 wherein said dopant is platinum.

6. The device for purifying air of claim 1 further comprising a means for controlling humidity in said reactor.

7. The device for purifying air of claim 1 further comprising a fibrous mass located in said reactor, said fibrous mass holding said photocatalyst.

8. The device for purifying air of claim 7 wherein said fibrous mass is fiber glass.

9. The device for purifying air of claim 1 wherein said ultraviolet light source emits light of wavelength shorter than 387 nanometers.

10. A compact device with a base and a top for purifying air that is plugged directly into a wall power outlet comprising a set of power prongs protruding from the device for plugging into the wall outlet, a compartment containing a photocatalyst that is illuminated by an ultraviolet light source, an opening at the base of the device for air to enter, a heater means in the device near this opening for heating air entering the device and causing this air to rise past the illuminated photocatalyst, the air becoming purified, and an exit port at the top of the device for the purified air to exit.

11. The compact device of claim 10 where the photocatalyst is primarily titanium dioxide.

12. The compact device of claim 11 where the titanium dioxide is doped with platinum.

13. The compact device of claim 11 where the ultraviolet light source emits light of wavelength shorter than 400 nanometers.

14. The compact device of claim 13 where the ultraviolet light source emits light of wavelength longer than 350 nanometers, the light source also producing visible light.

15. The compact device of claim 14 further comprising a means for allowing the visible light to escape.

16. A device for purifying air comprising:

a chimney with a base and top;

a photocatalyst located in said chimney;

an ultraviolet light source located in said chimney, said ultraviolet source illuminating said photocatalyst with ultraviolet light of wavelength shorter than 387 nanometers, said ultraviolet light source also producing visible light;

a heater means located at the base of said chimney for drawing air into said chimney by convection and causing air to rise past said photocatalyst, said air being expelled from the top of said chimney;

a means for allowing said visible light to escape from said chimney.

* * * * *